US00PP33350P2

(12) United States Plant Patent
Olesen

(10) Patent No.: US PP33,350 P2
(45) Date of Patent: Aug. 17, 2021

(54) MINIATURE ROSE PLANT NAMED 'POULPAR 121'

(50) Latin Name: *Rosa hybrida*
Varietal Denomination: Poulpar121

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 16/974,005

(22) Filed: Sep. 3, 2020

(51) Int. Cl.
*A01H 5/02* (2018.01)
*A01H 6/74* (2018.01)

(52) U.S. Cl.
USPC ..... Plt./121

(58) Field of Classification Search
USPC ..... Plt./101, 116, 121
See application file for complete search history.

(56) References Cited

PUBLICATIONS https://www.poulsenroser.dk/en/roses/ShowProduct/69351, (Retrieved from the Internet on Jan. 27, 2021, 'Gulla', 2 pages total).*

* cited by examiner

*Primary Examiner* — Susan McCormick Ewoldt

(57) ABSTRACT

A new garden rose plant of the Miniature class which has abundant, mauve-pink flowers and attractive foliage. This new and distinct variety has shown to be uniform and stable in the resulting generations from asexual propagation.

2 Drawing Sheets

Botanical designation: *Rosa hybrida.*
Variety denomination: 'Poulpar121'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulpar121', originated as a single seedling from the stated cross.

The new variety may be distinguished from its male pollen parent and female seed parent primarily by the following characteristics. The male pollen parent plant has light lavender purple flowers while the new variety has mauve-pink flowers. The female seed parent plant has pink flowers while the new variety has mauve-pink flowers.

The objective of the hybridization of this rose variety was to create a new and distinct variety with unique qualities, such as:

1. Uniform and abundant mauve-pink flowers;
2. Vigorous, but compact growth when propagated on its own roots;
3. Exceptional disease resistance.

This combination of qualities is not present in previously available commercial cultivars of this type, known to the inventor, and distinguish 'Poulpar121' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulpar121' was selected in the spring of 2014 by the inventor as a single plant from the progeny of the aforementioned hybridization.

Asexual reproduction of 'Poulpar121' by rooted cuttings was first done by Mogens N. Olesen in the nursery in Fredensborg, Denmark in July, 2014. This initial and other subsequent asexual propagations conducted in controlled environments have demonstrated that the characteristics of 'Poulpar121' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar121'.

Specifically illustrated in FIG. 1 of the drawings are open flowers viewed from above and from the side, sepals and petals detached revealing reproductive flower parts, and a cluster of open flowers on the branch.

Figure 1:
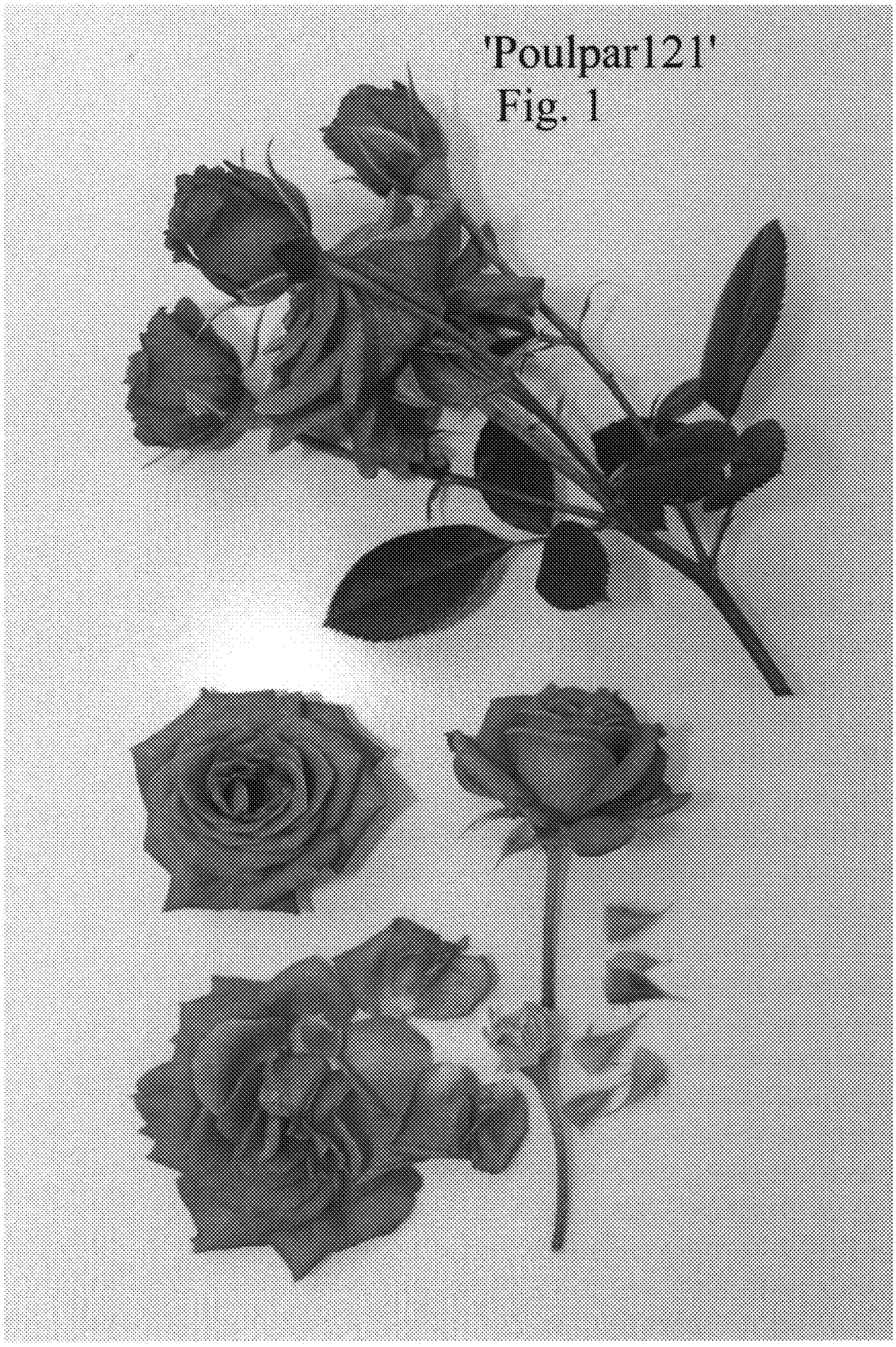
Figure 2:
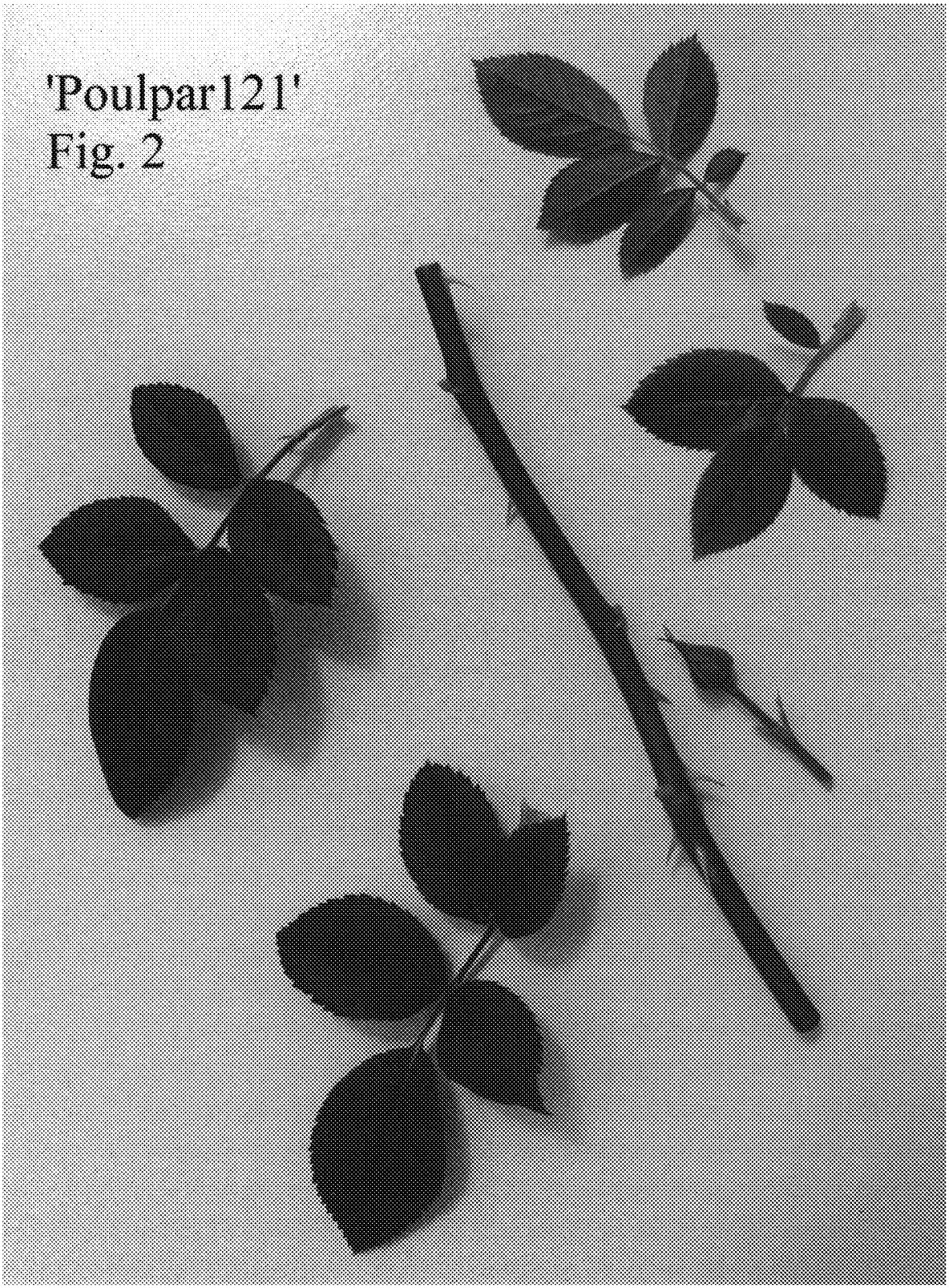

Specifically illustrated in FIG. 2 of the drawings are flower bud, bare stem, juvenile and mature leaves. Plants shown are 4 months of age.

DETAILED DESCRIPTION OF THE VARIETY

The following is a description of 'Poulpar121', as observed in its growth in a controlled environment greenhouse in Odense Denmark. Observed plants are 4 months old and were grown on their own roots in 19 cm containers. Color references are made using The Royal Horticultural Society (London, England) Colour Chart, 2001, except where common terms of color are used.

For a comparison, several physical characteristics of the rose variety 'Poulpar097', U.S. Plant Pat. No. 29,120 are compared to 'Poulpar121' in Chart 1.

CHART 1

| | 'Poulpar121' | 'Poulpar097' |
|---|---|---|
| Petal Count | 32 | 45 |
| Flower Diameter | 56 mm | 65 mm |
| General Tonality of Flower Color | Red-Purple Group 67A | Red-Purple Group N57C |

FLOWER AND FLOWER BUD

Blooming habit: Continuous.

Flower bud:

*Size.*—Upon opening, 20 mm in length from base of receptacle to end of bud. Bud diameter is 16 mm.

*Bud form.*—Ovoid with a broad base.

*Bud color.*—As sepals divide petals are Red- Purple Group 61B.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—5 mm long, 8 mm wide.

*Receptacle.*—Texture: Smooth. Size: 6 mm in height, 6 mm wide. Color: Yellow-Green Group 144A. Shape: Funnel.

*Pedicel.*—Surface: Smooth with abundant stipitate glands. Length: About 32 mm. Diameter: 3 mm on average. Color: Yellow-Green Group 144A. Strength: Strong.

*Peduncle.*—Length: 2 to 5 cm. Diameter: About 3 mm. Color: Yellow-Green Group 145A. Texture: Smooth.

Flower bud development: Flower buds are borne in clusters of about 5 flower buds per stem.

Flower bloom:

*Fragrance.*—Light floral scent.

*Duration.*—The blooms have a duration on the plant of approximately 21 days. Petals fall cleanly away from plant after flowers have fully matured.

*Size.*—Flower diameter is 56 mm when open. Flower depth is 23 mm.

*Flower shape.*—High centered double with a high pointed center which is tightly closed.

*Shape of flower, side view.*—The upper portion is flat. The lower portion is a flattened concave.

Petalage: Under normal conditions, flowers have about 32 petals.

General tonality of flower: Open flowers are Red-Purple Group 67A.

Petal color:

*Upon opening, outer petals.*—Upper surface: Red-Purple Group 67A splashed with Red-Purple Group 65A. Lower surface: Red-Purple Group 68B splashed with Red-Purple Group 67A.

*Upon opening, inner petals.*—Upper surface: Red-Purple Group 67A splashed with Red-Purple Group 65A. Lower surface: Red-Purple Group 68B splashed with Red-Purple Group 67A.

*Basal petal spots, upon opening.*—Upper surface: Yellow Group 4D. Lower surface: White Group 155A.

*After opening, outer petals.*—Upper surface: Red-Purple Group 67A splashed with Red-Purple Group 65A. Lower surface: Red-Purple Group 68B splashed with Red-Purple Group 67A.

*After opening, inner petals.*—Upper surface: Red-Purple Group 67A splashed with Red-Purple Group 65A. Lower surface: Red-Purple Group 68B splashed with Red-Purple Group 67A.

*Basal petal spots, after opening.*—Upper surface: Yellow Group 4D. Lower surface: White Group 155A.

Petals:

*Petal reflex.*—Strong.

*Margin.*—Entire and uniform. Light undulations.

*Shape.*—Broad and elliptic. Apex shape: Rounded. Base shape: Acute.

*Size.*—30 mm (l)×32 mm (w).

*Texture.*—Smooth.

*Thickness.*—Average.

Petaloids:

*Size.*—10 mm (l) by 8 mm (w).

*Quantity.*—About 4.

*Shape.*—Elliptical with an acute base and rounded apices.

*Color.*—The upper side is Red-Purple Group 67A splashed with Red-Purple Group 65A with a petaloid basal spot of Yellow Group 4D. The lower side is Red-Purple Group 68B splashed with Red-Purple Group 67A with a petaloid spot at the base of White Group 155A.

Reproductive flower parts:

*Pollen.*—None observed.

*Anthers.*—Size: 3 mm in length. Color: Yellow Group 11C. Quantity: 38 on average.

*Filaments.*—Color: Yellow Group 8B. Length: 5 mm.

*Pistils.*—Length: 6 mm. Quantity: 27 on average.

*Stigmas.*—Color: Greyed-Yellow Group 160D.

*Styles.*—Color: Red-Purple Group N57A.

*Location of stigmas.*—Superior in location relative to the length of the filaments and the height of the anthers.

*Hips.*—None Observed.

PLANT

Plant growth: Upright and compact. Plants are 65 cm in height, and 50 cm wide.

Stems:

*Color of juvenile growth.*—Yellow-Green Group 144B.

*Color of mature growth.*—Yellow-Green Group 144A.

*Length.*—Canes are about 35 cm from the base of the plant to the flowering portion.

*Diameter.*—About 5 mm.

*Internodes.*—On mature canes about 40 mm between nodes.

*Surface texture.*—Young wood: Smooth. Older wood: Smooth.

Long prickles:

*Incidence.*—7 prickles per 10 cm of stem.

*Size.*—Average length of prickles on mature stems is 8 mm.

*Shape.*—Upper portion is linear. Lower portion is deep concave.

*Color*.—Juvenile prickles: Greyed-Yellow Group 160D. Mature prickles: Greyed-Yellow Group 160D.

Plant foliage:

*Compound leaf*.—90 mm (l)×58 (w).

*Quantity*.—2 leaves per 10 cm of stem on average.

*Leaf bearing angle to the stem*.—45 degrees.

*Color of juvenile foliage*.—Upper side: Yellow-Green Group 144A. Lower side: Yellow-Green Group 144B.

*Color of mature foliage*.—Upper side: Yellow-Green Group 146A. Lower side: Yellow-Green Group 147B.

Plant leaves and leaflets:

*Stipules*.—Size: 7 mm long, 3 mm wide. Quantity: 2 per compound leaf. Shape: Linear, slightly broad based with outward extending apices. Margins: Finely serrated. Color: Yellow-Green Group 147A.

*Petiole*.—Length: 10 mm. Diameter: 2 mm. Upper surface color: Yellow-Green Group 146A. Lower surface color: Yellow-Green Group 145A.

*Rachis*.—Length: 32 mm. Upper surface color: Yellow-Green Group 146A. Lower surface color: Yellow-Green Group 145A.

*Leaflet*.—Quantity: Normally 5 to 7 leaflets. Margins: Serrated. Size: Terminal leaflets are about 41 mm long, 25 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar121', substantially as illustrated and described herein, due to its abundant mauve-pink flowers, disease resistance, and extended period of bloom.

* * * * *

'Poulpar121'

'Poulpar121'